(12) United States Patent
Coroneo

(10) Patent No.: US 9,693,893 B2
(45) Date of Patent: Jul. 4, 2017

(54) INTRAVITREAL INJECTION DEVICE AND METHOD

(76) Inventor: Minas Theodore Coroneo, Vaucluse (AU)

(*) Notice: Subject to any disclaimer, the term of this patent is extended or adjusted under 35 U.S.C. 154(b) by 918 days.

(21) Appl. No.: 13/510,917

(22) PCT Filed: Nov. 19, 2010

(86) PCT No.: PCT/AU2010/001554
§ 371 (c)(1),
(2), (4) Date: Oct. 5, 2012

(87) PCT Pub. No.: WO2011/060498
PCT Pub. Date: May 26, 2011

(65) Prior Publication Data
US 2013/0023824 A1    Jan. 24, 2013

(30) Foreign Application Priority Data
Nov. 20, 2009    (AU) ................................ 2009905700

(51) Int. Cl.
*A61M 5/42*    (2006.01)
*A61F 9/00*    (2006.01)

(52) U.S. Cl.
CPC .................... *A61F 9/0017* (2013.01)

(58) Field of Classification Search
CPC ............ A61F 9/0026; A61F 2009/0052; A61F 9/013; A61F 9/0136; A61F 9/007
USPC .......................................... 604/116
See application file for complete search history.

(56) References Cited

U.S. PATENT DOCUMENTS

| 4,739,761 | A | * | 4/1988 | Grandon | A61F 9/0136 606/166 |
| 6,508,793 | B1 | * | 1/2003 | Harrold | A61F 9/0008 604/294 |
| 2008/0033351 | A1 | * | 2/2008 | Trogden | A61F 9/0017 604/57 |
| 2009/0043322 | A1 | | 2/2009 | Melki | |
| 2009/0123527 | A1 | * | 5/2009 | Alam | A61K 9/0048 424/449 |
| 2009/0259204 | A1 | * | 10/2009 | Galdeti | A61M 35/003 604/302 |

FOREIGN PATENT DOCUMENTS

| DE | 102005002465 | | 7/2006 | |
| DE | 102005002465 A1 | | 7/2006 | |
| FR | 2693368 A1 | | 1/1994 | |
| NL | WO 2008097072 A1 | * | 8/2008 | .......... A61F 9/0017 |
| WO | 96/06584 A1 | | 3/1996 | |

OTHER PUBLICATIONS

International Search Report and Written Opinion issued on Jan. 18, 2011 for International Application No. PCT/AU2010/001554.

\* cited by examiner

*Primary Examiner* — Laura Bouchelle
(74) *Attorney, Agent, or Firm* — Knobbe, Martens, Olson & Bear, LLP

(57) ABSTRACT

A device for use during an intravitreal injection procedure, the device including: a main body portion with a handle at one end for holding the device; and, a contact portion at the other end for contacting the surface of an eye; wherein the contact portion includes a distance indicator for indicating a pre-determined distance from a reference point on the eye.

21 Claims, 6 Drawing Sheets

INTRAVITREAL INJECTION DEVICE AND METHOD

The present invention relates to a device for use during an intravitreal injection procedure and a method of using the device.

BACKGROUND

Intravitreal injection as a minimally invasive procedure that has become an effective intervention in the management of numerous eye diseases. The procedure involves an active substance being directly injected into the vitreous cavity of the eye of a patient. Typically, the procedure is only used when the active substance does not easily penetrate into the eye, when applied by other means (such as topical or systemic), and where the active substance, or its vehicle, is not toxic to the intraocular tissue. The procedure bypasses anatomical barriers in the eye.

Intravitreal injection with administration of various agents has become a mainstay of treatment of conditions such as endopthalmitis, viral retinitis, age-related macular degeneration, cystoid macular edema, diabetic retinopathy, uveitis, vascular occlusions, and retinal detachment. The most common example of when an intravitreal injection procedure is necessary is in the treatment of neovascular age-related macular degeneration with antivascular endothelial growth factor therapy. Antimicrobial intravitreal injections are also used to treat sight threatening intraocular infections such as endophthalmitis and cytomegalovirus retinitis in patients with the acquired immunodeficiency syndrome (AIDS).

The procedure of intravitreal injection is highly relevant in that macular degeneration is a leading cause of blindness in many societies. In developing regions of the world with limited financial resources for health care, the HIV/AIDS pandemic continues to unfold, and it may well be that cytomegalovirus retinitis will contribute significantly to world blindness. It is considered that at this time, the only viable treatment option in resource poor settings is injection of antiviral drugs via an intravitreal injection procedure.

Prior to injecting an active substance in to the intraocular tissue of the eye, the patient is given anaesthetic (topical and sometimes subconjunctival) to provide the required anaesthesia for sufficient patient comfort throughout the intravitreal injection procedure. A topical disinfectant, such as povidone iodine (and sometimes antibiotic), is then applied followed by the application of a mercury bag on top of the eye for 10 to 15 minutes to decompress and soften the globe which will reduce any intraocular pressure rise resulting from the subsequent injection.

A calliper set is then used to mark the injection site which is typically 3-4 mm from the limbus in the inferotemporal pars plana region of the eye. The syringe is then inserted at the injection site and aimed towards the mid-vitreous cavity after which the active is slowly injected. Topical antibiotics may be applied for 3 to 7 days post-injection.

In order to manage an intravitreal injection procedure, several instruments are needed all of which require sterilization prior to reuse. A speculum is needed to hold the eye open, a forcep is also used to hold and steady the eye during the injection as well as a set of callipers to measure the required distance from the limbus to the injection site. This level of instrumentation means that the person undertaking the intravitreal procedure must also have a significant degree of skill and experience with such medical procedures.

Accordingly, there is a need to provide a device for use during an intravitreal injection procedure, and/or a method of conducting an intravitreal injection procedure which reduces the number of instruments required during the procedure and/or reduces the complexity of the procedure.

SUMMARY

According to one aspect the present invention provides a device for use during an intravitreal injection procedure, the device including:
 a main body portion with a handle at one end for holding the device;
 a contact portion at the other end for contacting the surface of an eye; wherein the contact portion includes a distance indicator for indicating a pre-determined distance from a reference point on the eye.

In one form the reference point on the eye is the corneoscleral junction hereinafter referred to as the limbus.

In one form the indicated pre-determined distance identifies an injection site for the intravitreal injection procedure. In one form the identified injection site is adjacent the distance indicator.

In one form the contact portion includes an under surface for contacting the conjunctiva of the eye. In one form, the under surface includes one or more raised portions to hold the contact portion of the device in position on the conjunctiva of the eye. In another form, the one or more raised portions are in the form of a plurality of teeth. In one form, the plurality of teeth is sufficiently raised to hold the device in position on the conjunctiva during an intravitreal injection without tearing the conjunctiva. In one form, each of the plurality of teeth are in the form of square or triangular pyramid portions.

In one form, the contact portion is substantially planar and includes the distance indicator on an upper surface. In use, an edge of the contact portion may be aligned with the limbus of the eye wherein the distance indicator indicates the pre-determined distance from the limbus. In one form, the distance indicator provides 1 mm increments of distance from the limbus when the edge of the contact portion is aligned with the limbus of the eye. In this form, the distance indicator provides 3 to 7 times 1 mm increments from the limbus when the edge of the contact portion is aligned with the limbus of the eye.

In another form, the distance indicator provides one prominent marking at the predetermined distance from the limbus that is most frequently used in an intravitreal injection procedure. Such a distance may be 3 mm, 3.5 mm, 4 mm or 4.5 mm from the limbus.

In one form, the main body portion is in the form of an elongate rod with the handle at one end. In this form, the under surface of the contact portion is at an obtuse angle of orientation relative to the main body portion. In this form, the obtuse angle is between 105° and 150°. In a preferred form, the obtuse angle is approximately 135°.

In one form, the device is composed of a surgical grade material. In one form, the surgical grade material may be disposable, such as for example plastic.

In another form, the handle of the device has an absorbent contact point attached at the distal end from the contact portion. In one form, the absorbent contact point is in the form of a cotton bud, or cotton tip. The absorbent contact point may be used to apply anaesthetic to the injection site and/or the absorbent contact point may be held over the injection site to minimize reflux of the injected substance.

According to another aspect the present invention provides a method of using a device during an intravitreal injection procedure, the device including: a main body portion with a handle at one end for holding the device; a contact portion at the other end for contacting the surface of an eye; wherein the contact portion includes a distance indicator for indicating a pre-determined distance from a reference point on the eye, wherein the method includes the following steps:

a. holding the device whereby the contact portion is able to contact the surface of the eye;
b. positioning the contact portion whereby the distance indicator provides a pre-determined distance point from a reference point on the eye; and,
c. conducting an intravitreal injection at the pre-determined distance point.

BRIEF DESCRIPTION OF THE ACCOMPANYING FIGURES

The present invention will become better understood from the following detailed description of various non-limiting embodiments thereof, described in connection with the accompanying figures, wherein.

Figure 5:
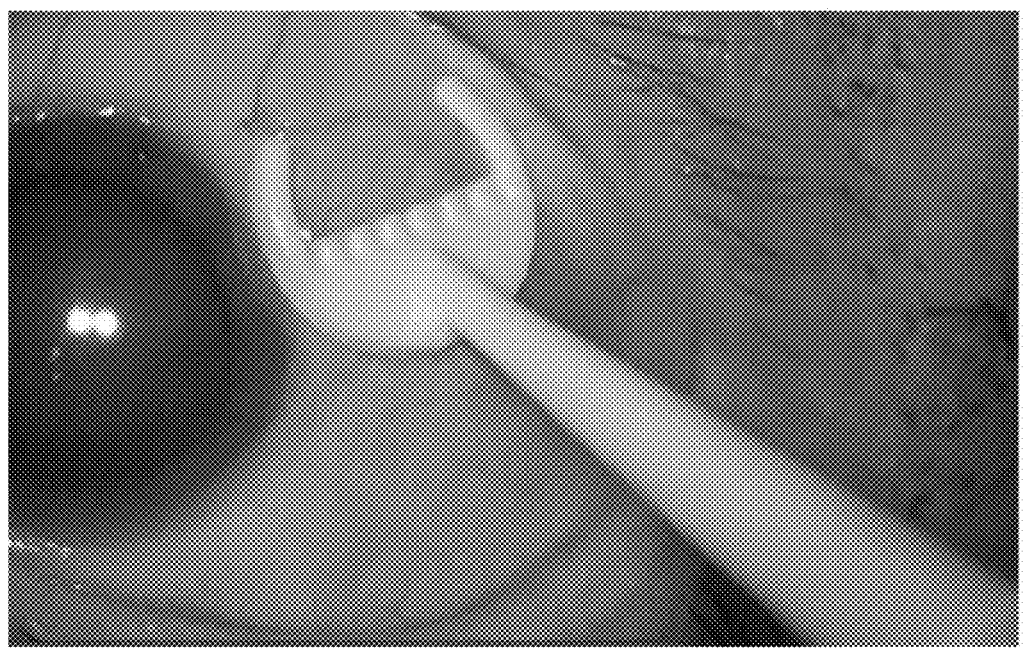
Figure 6:
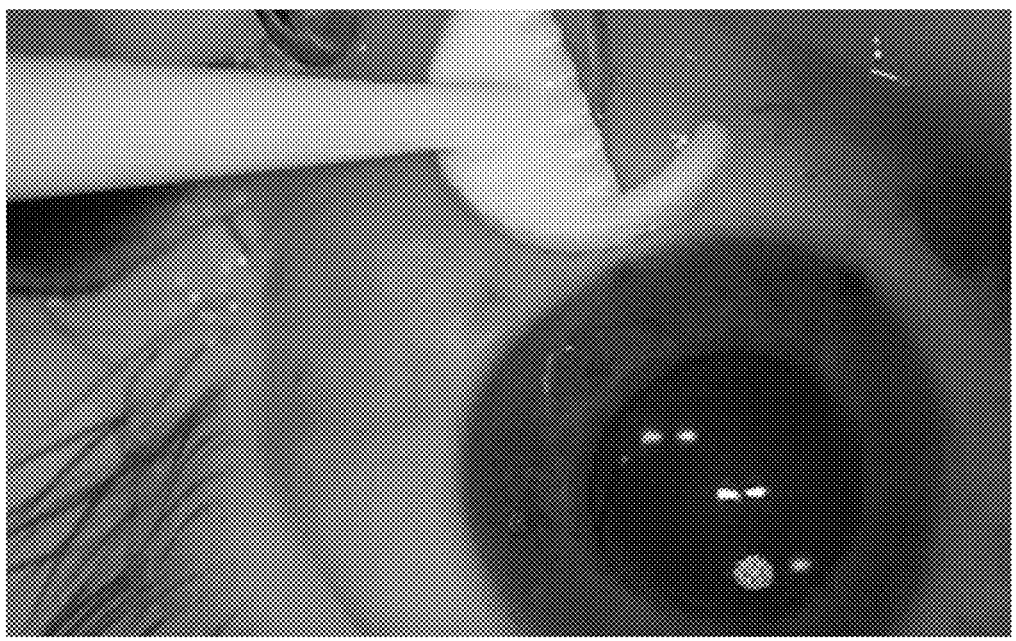

FIG. 5 is photograph of a device in accordance with another aspect of the present invention in contact with the conjunctiva of an eye with the edge of the device in contact with the limbus (that acts as a measurement reference point); and, FIG. 6 is a photograph of a device in accordance with another aspect of the present invention in contact with the conjunctiva of an eye and aligned with the limbus during a intravitreal injection procedure.

DETAILED DESCRIPTION OF EMBODIMENTS AND THE ACCOMPANYING FIGURES

The foregoing describes only some embodiments of the present invention, and modifications and/or changes can be made thereto without departing from the scope and spirit of the invention, the embodiments being illustrative and not restrictive.

In the context of this specification, the word "comprising" means "including principally but not necessarily solely" or "having" or "including", and not "consisting only of".

Variations of the word "comprising", such as "comprise" and "comprises" have correspondingly varied meanings.

Figure 1:
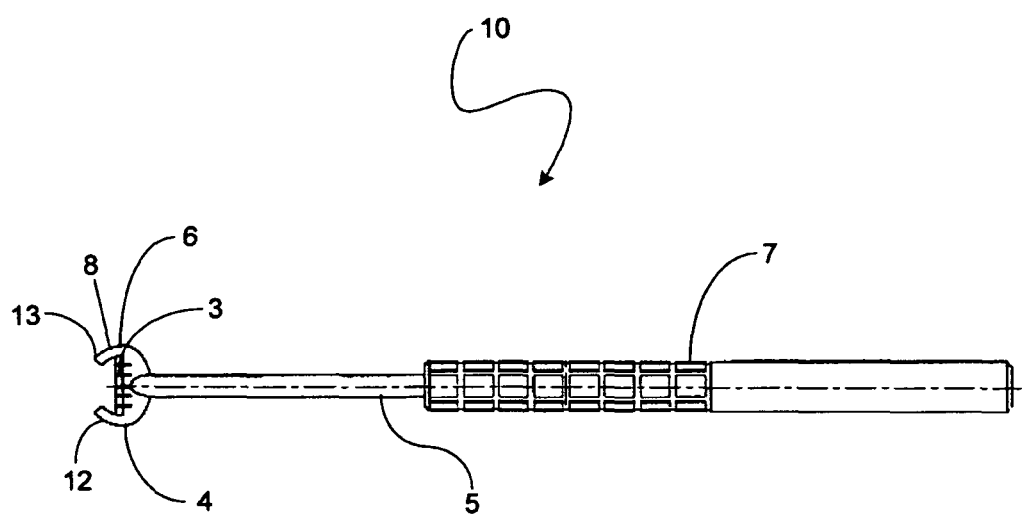
FIG. 1 is a plan view of an embodiment of a device in accordance with one aspect of the present invention.
Figure 2:
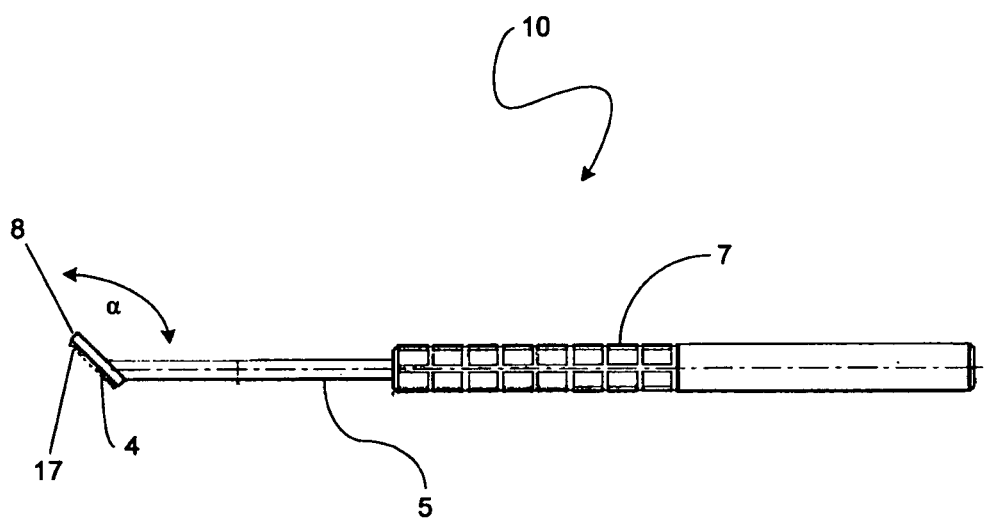
FIG. 2 is a side elevation of the embodiment of FIG. 1.

Referring now to FIGS. 1 and 2 there are shown two different views of a device in accordance with one embodiment of the present invention for use during an intravitreal injection procedure. The device 10 consists of a main body portion 5 with a handle 7 at one end of the main body portion 5 for holding the device in the hand of a person who is typically performing the intravitreal injection procedure. At the other end of the main body portion 5 there is a contact portion 8 for contacting the conjunctiva of the eye. The contact portion 8 also includes a distance indicator 3 which enables a distance to be measured from a reference point on the eye in order to identify an injection site for the intravitreal injection procedure. The specific point for the injection site is calculated when either the right 6 or left edge 4 of the contact portion 8 are aligned with a particular reference point on the conjunctiva of the eye.

In the present embodiment the right 6 or left edge 4 of the contact portion 8 is aligned with a reference point which may be the edge of the limbus of the eye which enables a distance to be calculated along the distance indicator 3 in a radial direction in millimeters away from the limbal margin. Once a distance away from the limbus is identified this provides an injection site which may be used to conduct an intravitreal injection whilst maintaining the device 10 on the surface of the conjunctiva. Typically, an injection site may be located at a radial distance of 3-4 mm from the edge of the limbus.

The under surface of the contact portion 8 includes a plurality of raised portions 17 which enable the device 10 to be held on the conjunctiva in a steady location without tearing or otherwise damaging the surface of the conjunctiva.

In addition to the distance indicator 3, the contact portion 8 also includes arms 12 and 13 which extend around from the distance indicator providing a general annulus shape for contacting the eye except for a break between the tips of the arms 12 and 13. The additional arms 12 and 13 of the contact portion 8 provide further contact regions in order to steady the device 10 on the conjunctiva, which provides additional stability whilst the intravitreal injection is taking place.

As can be seen specifically from FIG. 2, the contact portion 8 is at an obtuse angle α to the main body portion 5. Such an obtuse angle α, provides that the device 10 may be used at the same time as performing an intravitreal injection and allow space for the syringe to be operated while still maintain the device 10 in contact with and in position "gripping" the conjunctiva. The angle α may be any suitable obtuse angle which still provides sufficient room to operate a syringe whilst still providing sufficient down force to hold the device 10 in position on the conjunctiva. In a preferred form the angle α is between 105° and 150° and in the present embodiment shown in FIG. 2 is approximately 135°.

Figure 3:
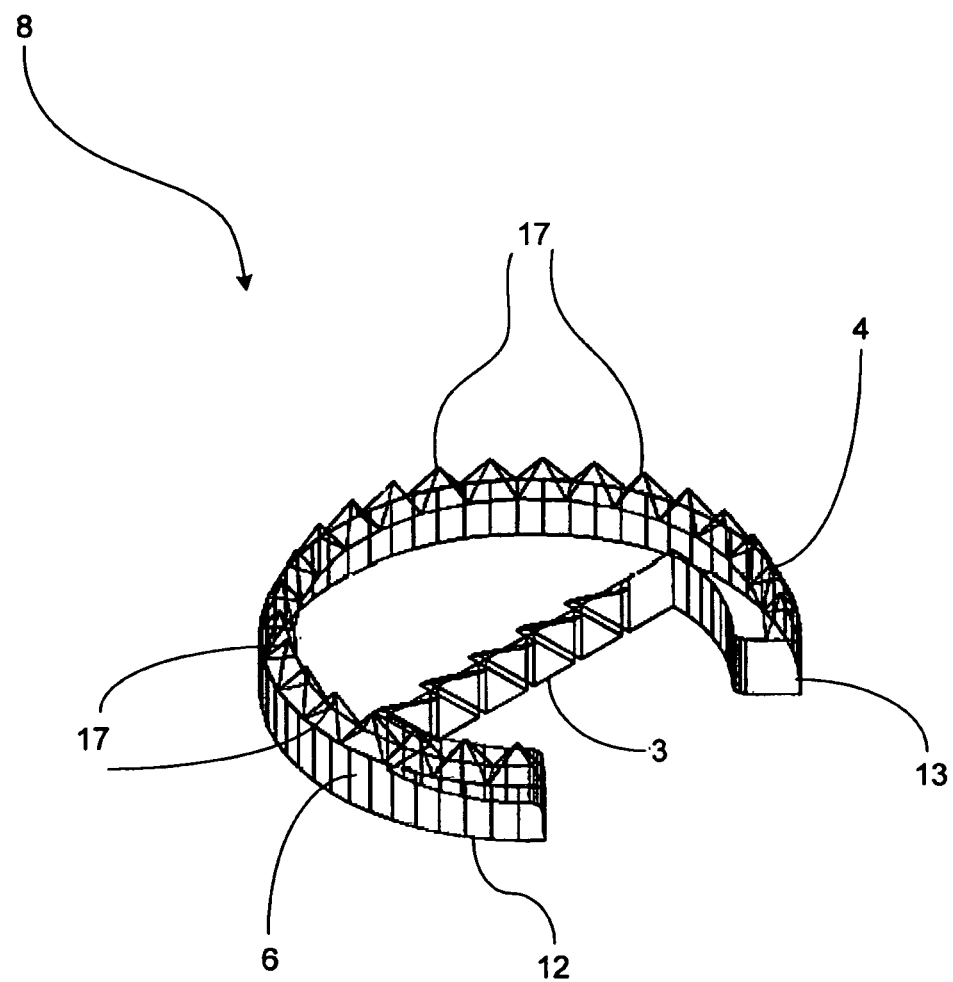
FIG. 3 is an underneath perspective view of the contact portion of a device in accordance with one aspect of the present invention.
Figure 4:
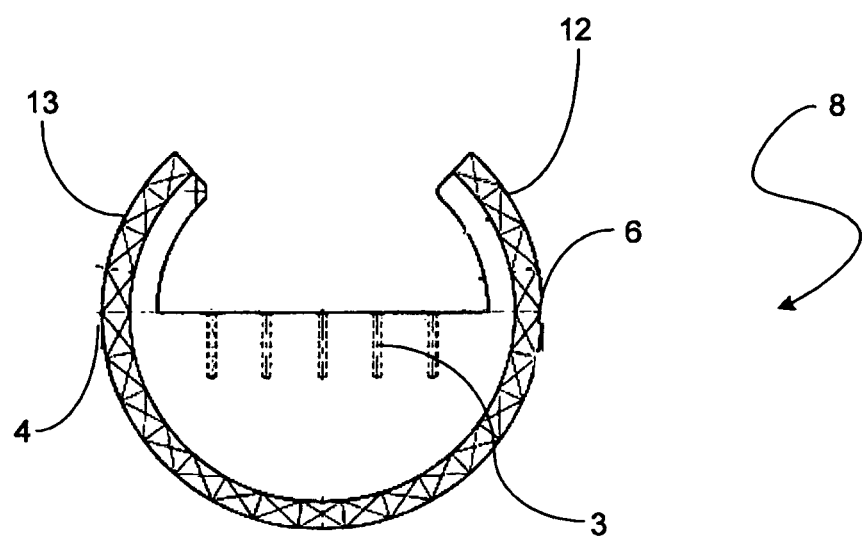
FIG. 4 is a plan view of the contact portion of a device in accordance with one aspect of the present invention.

Referring to FIGS. 3 and 4, the protrusions 17 on the underside of the contact portion 8 can be seen and are located around the periphery of the contact portion 8. The protrusions 17 are in the form of triangular indents which in the present case are in the shape of small quadrilateral pyramids. These protrusions 17 are sufficiently small and do not include a sufficiently sharp point whereby they maintain the device 10 on the conjunctiva without tearing the tissue of the eye.

The device of the present invention provides that two if not three of the instruments typically required for an intravitreal injection procedure may be replaced by the device of the present invention.

The contact portion of the device of the present invention is based on a semicircular ring including a plurality of raised portions in the form of fine teeth on the bottom surface of the contact portion which effectively grip the surface of the conjunctiva without tearing it when contacting the eye of the patient.

In use, an edge of the contact portion is aligned with the edge of the limbus, or the limbal margin, and a millimeter scale, or distance indicator, appearing on the upper face of the contact portion allows measurement of the distance in a radial direction away from the limbus. This allows that an injection site can be identified a specific distance away from the edge of the limbus wherein the syringe needle may then be inserted at the injection site from the limbus through the pars plana and the injection completed.

Although not shown in the figures, the end of the handle of the device at a distal point from the contact portion may also include an absorbent contact portion which may be in the form of a cotton bud or cotton tip. The absorbent contact point may be used to apply anaesthetic to the injection site and/or the absorbent contact point may be held over the injection site to minimize reflux of the injected substance.

An embodiment of the device can be seen in the photographs included at FIG. 5 and FIG. 6 in which the contact portion of the device in accordance with one aspect of the present invention is aligned with the edge of the limbus. In FIG. 5, the left edge of the contact portion of the device is aligned with the right edge of the limbus thereby identifying an injection site at a radial distance from the edge of the limbus along the distance indicator displayed in millimeters on the upper face of the contact portion. As an alternative, FIG. 6 shows the right edge of the contact portion of the device aligned with the left edge of the limbus identifying an injection site at a radial distance from the edge of the limbus along the distance indicator at which point the tip of the needle can be seen ready to proceed with an injection at the identified injection site.

Although a speculum is shown in FIG. 6 assisting to maintain the eye of the patient in an open state, this can be dispensed with, as the perimeter of the contact portion helps to keep the eyelids away from the injection site. The device in accordance with the present invention may prove to be useful as a time saver in both developed and developing countries and may allow trained nursing staff or health workers to carry out these injections given the reduction of instrumentation and level of complexity provided by with the use of the device in an intravitreal injection procedure.

Many modifications will be apparent to those skilled in the art without departing from the scope of the present invention. It will be appreciated that various forms of the invention may be used individually or in combination.

The invention claimed is:

1. A device for use during an intravitreal injection procedure, the device comprising:
    a main body portion with a handle at one end for holding the device; and
    a contact portion at the other end configured to contact a surface of a human eye; wherein the contact portion is a generally annulus shape that comprises:
        a distance indicator region bounded by a line that intersects the annulus shape at two points and an arc of the annulus shape, wherein the distance indicator region is in the same plane as the annulus shape, wherein the distance indicator region is configured to indicate a pre-determined distance from a reference point on the eye, wherein the distance indicator region comprises a plurality of markings perpendicular to the line that intersects the annulus shape, and wherein the plurality of markings denote consecutive 1 mm increments of distance from the reference point of the eye, and
        two arms of the annulus shape that extend around from and in the same plane as the distance indicator region, except for a break between tips of the arms, wherein the two arms and the distance indicator region collectively provide the general annulus shape that otherwise surrounds an unobstructed opening within the general annulus shape, wherein the opening is configured to permit passage of an injector through the opening.

2. A device according to claim 1 wherein the reference point on the eye is a limbus.

3. A device according to claim 2 wherein, when an edge of the contact portion is aligned with the limbus of the eye, the distance indicator region indicates the predetermined distance from the limbus.

4. A device according to claim 1 wherein the indicated pre-determined distance identifies an injection site for the intravitreal injection procedure.

5. A device according to claim 1 wherein the contact portion includes an under surface for contacting a conjunctiva of the eye.

6. A device according to claim 5 wherein the under surface includes one or more raised portions to hold the contact portion of the device in position on the conjunctiva of the eye.

7. A device according to claim 6 wherein the one or more raised portions are in the form of a plurality of teeth.

8. A device according to claim 6 wherein one or more raised portions sufficiently raised to hold the device in position on the conjunctiva during an intravitreal injection without tearing or otherwise damaging the conjunctiva.

9. A device according to claim 6 wherein the one or more raised portions are in the form of square or triangular pyramids.

10. A device according to claim 5 wherein the under surface of the contact portion is at an obtuse angle of orientation relative to the main body portion.

11. A device according to claim 10 wherein the obtuse angle is between 105° and 150°.

12. A device according to claim 10 wherein the obtuse angle is approximately 135°.

13. A device according to claim 1 wherein the contact portion is substantially planar and includes the distance indicator region on an upper surface of the contact portion.

14. A device according to claim 1 wherein the distance indicator region includes 3 to 7 times 1 mm increments the reference point of the eye.

15. A device according to claim 1 wherein the main body portion is in the form of an elongate rod.

16. A device according to claim 1 wherein the device is composed of a surgical grade material.

17. A device according to claim 1 wherein the device is composed of a plastic material.

18. A device according to claim 1 wherein the handle of the device includes an absorbent contact point attached at a distal end from the contact portion.

19. A device according to claim 18 wherein the absorbent contact point is in the form of a natural or synthetic cotton bud, or cotton tip.

20. A device according to claim 18 wherein the absorbent contact point may be used to apply anaesthetic to an injection site and/or the absorbent contact point may be held over the injection site to minimize reflux of the injected substance during the intravitreal injection procedure.

21. A method of using a device according to claim 1 wherein the method includes the following steps:
    a. holding the device whereby the contact portion is able to contact the surface of the eye;
    b. positioning the contact portion whereby the distance indicator region provides a pre-determined distance point from a reference point on the eye thereby identifying an injection site; and,
    c. conducting an intravitreal injection at the injection site.

* * * * *